United States Patent

Arai

[11] 4,175,324
[45] Nov. 27, 1979

[54] DENTAL TREATMENT TOOL

[75] Inventor: Toshio Arai, Tokyo, Japan

[73] Assignee: Kabushiki Kaisha Morita Sanshoku, Japan

[21] Appl. No.: 819,507

[22] Filed: Jul. 26, 1977

[30] Foreign Application Priority Data

Jun. 23, 1977 [JP] Japan ............................ 52-82611[U]

[51] Int. Cl.² ............................ A61C 1/10; A61C 5/02
[52] U.S. Cl. .................................................... 433/122
[58] Field of Search ................... 32/33, 27, 57; 74/50, 74/750, 567, 568, 569, 570, 112, 116, 122, 124, 125

[56] References Cited

U.S. PATENT DOCUMENTS

| 610,987 | 9/1898 | Hendrickson et al. | 32/27 |
| 710,865 | 10/1902 | Hollender | 74/570 |
| 919,359 | 4/1909 | Jeffries et al. | 74/750 R |
| 1,711,846 | 5/1929 | Heilborn | 32/27 |
| 2,344,605 | 3/1944 | Droegkamp | 32/54 |
| 3,073,031 | 1/1963 | Brenman et al. | 32/46 |
| 3,164,903 | 1/1965 | Ellis | 32/27 |
| 3,967,380 | 7/1976 | Malata et al. | 32/57 |

FOREIGN PATENT DOCUMENTS 45-30435 10/1970 Japan .
51-40709 10/1976 Japan .

Primary Examiner—Robert Peschock
Assistant Examiner—Michael J. Foycik, Jr.
Attorney, Agent, or Firm—Wenderoth, Lind & Ponack

[57] ABSTRACT

An improved dental treatment tool includes a rotation shaft with an eccentric rotation plate having a drive pin thereon, and a vertically moving rotation cylinder for allowing a dental drill to move in vertical and horizontal directions. The rotation plate and the drive pin are engaged respectively with two portions of the vertically moving rotation cylinder so that the vertically moving rotation cylinder is automatically caused to rotate horizontally and move up and down, to thereby provide an excellent dental treating operation.

8 Claims, 4 Drawing Figures

DENTAL TREATMENT TOOL

BACKGROUND OF THE INVENTION

This invention relates to a dental treatment tool and more particularly to a dental tool which cuts a decayed tooth in the oral cavity with a vertical and horizontal motion of a dental drill.

In a conventional dental tool, a dental drill is only adapted to reciprocally move in a vertical direction to cut a portion of a carious tooth to be treated. However, the dental drill is not automatically allowed to move or cut in or along a plane facing the portion to be treated during a cutting operation. For this purpose, therefore, the dental drill is required to have a support, i.e. an outer casing handled manually to move the drill in a horizontal direction. This results in a decrease of efficiency in the cutting operation.

There has also been proposed another type of a dental treatment tool wherein a dental drill thereof is only able to reciprocally rotate in a horizontal plane unlike the former dental tool. According to the construction of this tool, ridges or grooves of the blade of the dental drill become choked up with cutting dust in the middle of a cutting operation. Accordingly, the dental drill must be moved up and down manually to avoid the filling of the cutting dust into the blade grooves thereof. This also results in poor efficiency of the dental treating operation.

Therefore, it is an object of the present invention to provide a dental treatment tool which automatically cuts along a plane simultaneously with a drilling cutting operation.

It is another object of the present invention to provide a dental treatment tool wherein no manual handling is required to move a dental drill vertically and horizontally.

It is a further object of the present invention to provide a dental treatment tool with which high efficiency is expected during a treating operation.

It is a still further object of the present invention to provide a dental treatment tool the construction of which is easy to manufacture and to maintain.

SUMMARY OF THE PRESENT INVENTION

According to the present invention, a dental treatment tool comprises a rotation shaft accommodated in an outer casing, a vertically moving rotation cylinder, and a support for a dental drill coupled with the cylinder, wherein the rotation shaft is provided with a rotation plate at the end thereof, the rotation axis of the rotation plate is eccentric with that of the rotation shaft and the rotation plate has a drive pin thereon positioned at a predetermined point other than the center thereof. The cylinder is positioned in a circular supporting member and is provided with a shoulder portion and a concave portion on a periphery surface thereof. The cylinder is caused to horizontally and reciprocally rotate within a limited angle and to move up and down with respective engagements of the rotation plate and drive pin with the shoulder and concave portion.

BRIEF DESCRIPTION OF THE DRAWINGS

The present invention will be more fully understood by reference to the following detailed description thereof, when read in conjunction with the attached drawings, wherein like reference numerals refer to like parts throughout the drawings, in which.

DETAILED DESCRIPTION OF THE PREFERRED EMBODIMENTS

Figure 1:
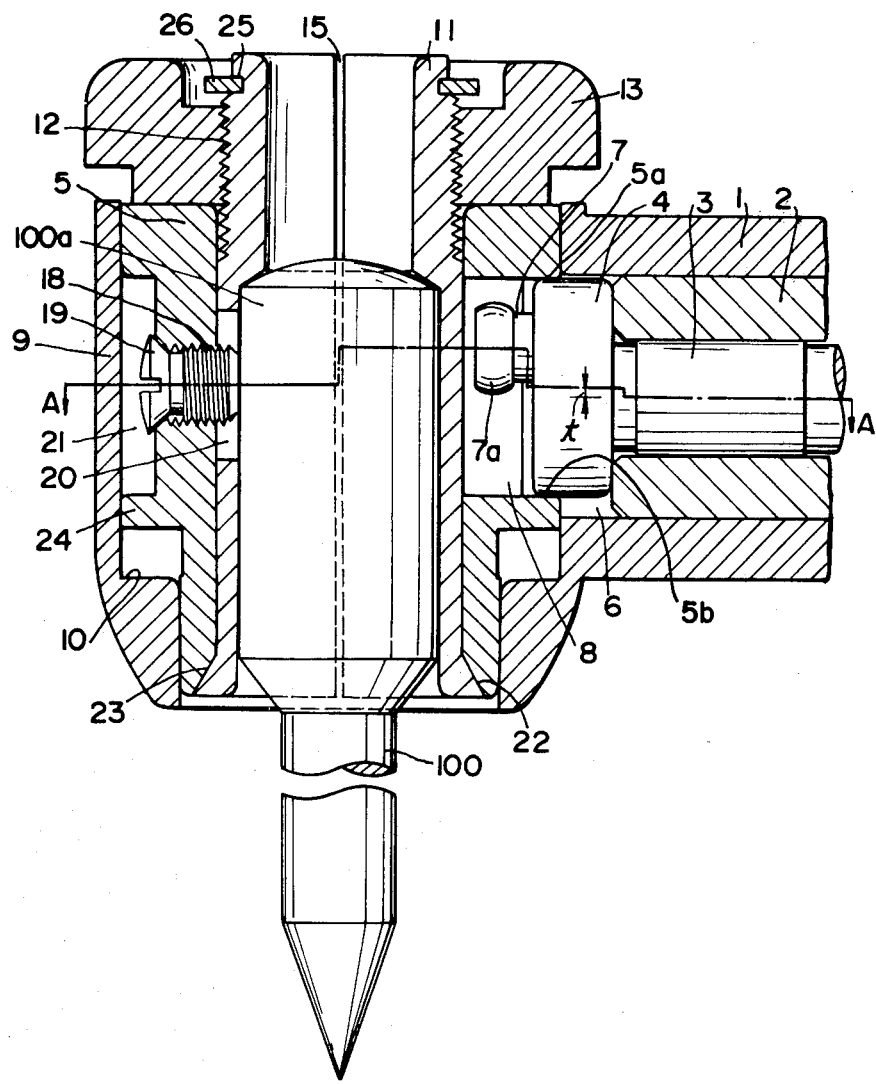
FIG. 1 is a cross sectional view illustrating an embodiment of a dental treatment tool according to the present invention.

With reference to FIG. 1, there is shown an embodiment of a dental treatment tool according to the present invention. A rotative force transmitting means comprises an outer casing 1, an inner casing 2 and a rotation shaft 3 rotatively accommodated therein. The rotation shaft 3 is caused to rotate in a predetermined direction with the rotation of a flexible rotation shaft (not shown) connected to a drive means such as a motor. The rotation shaft 3 is provided with a rotation plate 4 at the end thereof, the rotation axis of plate 4 being eccentric to the rotation axis of shaft 3. The rotation plate 4 is positioned in a space 6 formed between a vertically moving rotation cylinder 5 and the inner casing 2 and has a drive pin 7 thereon at a predetermined position other than the center thereof. The drive pin 7 has an arcuate or rounded surface forming a rotor 7a. The vertically moving rotation cylinder 5 is provided with a shoulder portion, defined by two axially spaced surfaces 5a and 5b, and a concave portion 8, defined by the surfaces 5a and 5b and by two axially extending, circumferentially spaced surfaces 8a and 8b. The shoulder portion and concave portion are respectively engaged by the rotation plate 4 and the drive pin 7, and cylinder 5 is positioned in a circular or cylindrical supporting member 9 which is integral with the outer casing 1. The circular supporting member 9 is provided with a stepped portion 10 therein (described hereinafter in detail) and has a support 11 for a dental drill 100. The support 11 for the dental drill is also coupled with a fastening nut 13 by means of threads 12. The support 11 is provided with three slits 15, 16 and 17 to render it resilient so that engagement is between the support 11 and the dental drill 100. One of the slits, preferably, the slit 15, may be formed continuously from the top of the support 11 to the bottom thereof, while the other slits 16 and 17 may stop in the middle thereof. The vertically moving rotation cylinder 5 is provided with a threaded aperture 18 for inserting a bolt 19 thereinto. The bolt 19 is passed through an aperture 20 of the support 11 to clamp a head portion 100a of the dental drill 100 so that the dental drill 100 is securely held in the support 11. A space 21 may be formed between the vertically moving rotation cylinder 5 and the circular supporting member 9 so that the motion of the former is not prevented by the head of the bolt 19. The support 11 is provided at the lower end thereof with an outwardly and downwardly expanding outer surface or protrusion 22. The protrusion 22 is adapted to engage with an outwardly and downwardly inclined surface 23 of the vertically moving rotation cylinder 5. This prevents the support 11 from being raised above a predetermined level. In addition, the vertically moving operation cylinder 5 is provided at a lower outer portion thereof with a flange 24 which abuts stepped portion 10 to prevent cylinder 5 from being lowered below a predetermined level. At the top of the support 11, there is provided an outer annular groove 25 into which is fitted a resilient fixed ring 26.

Figure 2:
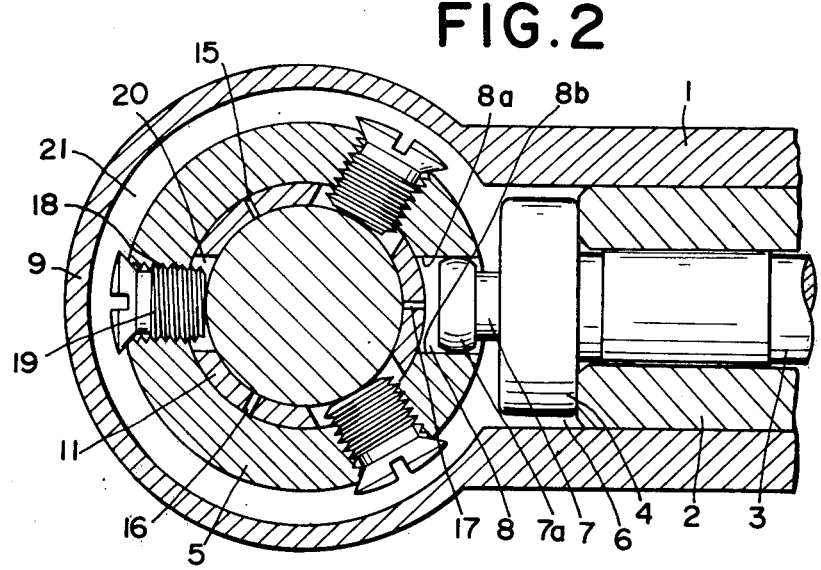
FIG. 2 is a cross sectional view taken along a line A—A in FIG. 1 and illustrating the dental treatment tool according to the present invention, wherein a vertically moving rotation cylinder thereof is shown in a first rotation position.
Figure 3:
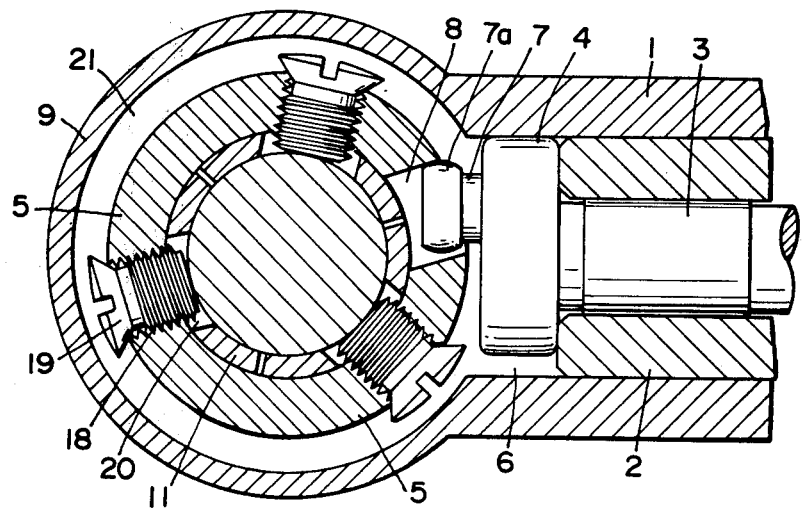
FIG. 3 is a cross sectional view identical to FIG. 2, but wherein the vertically moving rotation cylinder is shown in a second rotation position.
Figure 4:
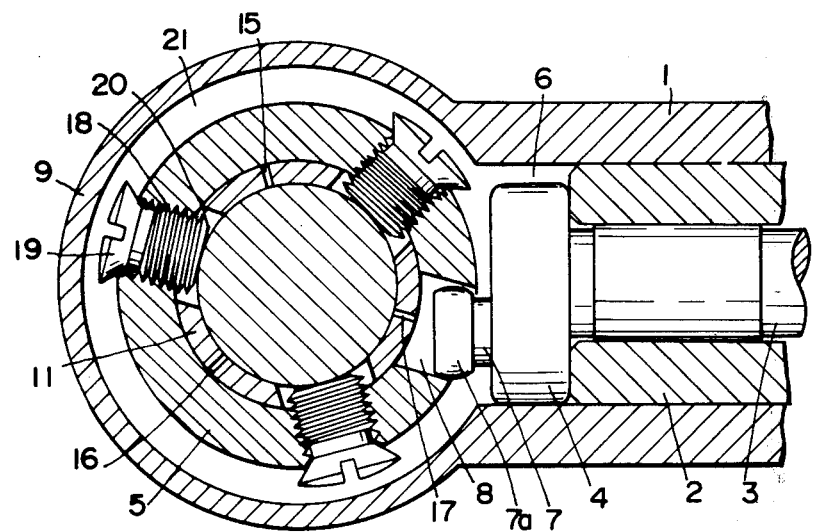
FIG. 4 is a cross sectional view identical to FIG. 2, but wherein the vertically moving rotation cylinder is shown in a third rotation position.

In operation, the rotation shaft 3 is caused to rotate in a predetermined direction with the rotation of a flexible rotation shaft connected to a motor as set forth above. This allows the rotation plate 4 to rotate in the same direction as that of the rotation shaft 3, because they are directly connected to each other. However, the rotation axis of the former is eccentric with respect to that of the latter by a predetermined dimension designated "t" so that the vertically moving rotation cylinder 5 is caused to move up and down due to the engagement thereof with the outer periphery of the eccentric rotation plate 4. If it is assumed that the dimension "t" is 0.2 mm, the vertically moving rotation cylinder 5 moves up and down by 0.4 mm. In addition, the relative horizontal position of the drive pin 7 is shifted, as shown in FIGS. 2 to 4 as the rotation plate 4 rotates. Thus, the vertically moving rotation cylinder 5 rotates reciprocally within a limited angle, for example, approximately 45°, due to engagement of the rotor 7a of drive pin 7 with cylinder 5. FIGS. 2 to 4 show that the vertically moving rotation cylinder 5 assumes first, second and third relatively rotated positions. Accordingly, the dental drill 100 is automatically allowed to horizontally rotate by the above mentioned angle and to simultaneously move up and down in accordance with the motion of the vertically moving rotation cylinder 5. As set forth above, the dental drill is caused to make vertical and horizontal movements, so that the cutting of a portion to be treated can be made efficiently and cutting dust can be prevented from filling into ridges of the drill during the horizontal movements thereof. Further, the horizontal rotation and the vertical motion of the vertically moving rotation cylinder 5 are smoothly made so that little noise occurs during a treating operation.

Although the present invention has been described with reference to a preferred embodiment thereof, many modifications and alterations may be made thereto within the spirit of the present invention.

What I claim is:

1. A dental treatment tool comprising:
   a casing;
   a rotation drive shaft supported in said casing for rotation about an axis of said drive shaft;
   a rotation cylinder supported in said casing for rotation about and axial movement along an axis of said rotation cylinder extending perpendicular to said axis of said drive shaft;
   said rotation cylinder including means for fixedly supporting a dentral drill;
   said rotation cylinder having therein, on the outer periphery thereof, a concave recess defined by two axially extending, circumferentially spaced surfaces;
   said rotation cylinder having extending from the outer periphery thereof two shoulders defined by axially spaced surfaces extending transverse to said rotation cylinder axis;
   said rotation drive shaft having integral with the inner end thereof a rotation plate having a diameter larger than that of said rotation drive shaft, said rotation plate having an axis eccentrically located with respect to said rotation drive shaft axis;
   said rotation plate being positioned between said two shoulders with an outer peripheral surface of said rotation plate in contact with both of said axially spaced surfaces of said shoulders, such that rotation of said rotation drive shaft will cause eccentric rotation of said rotation plate, and contact of said peripheral surface of said rotation plate with said shoulders of said rotation cylinder will cause reciprocating axial movement of said rotation cylinder with respect to said casing;
   said rotation plate having integral therewith and extending therefrom a drive pin having a rounded arcuate peripheral surface, said drive pin being located at a position other than the center of said rotation plate; and
   said drive pin being positioned within said concave recess with said rounded arcuate peripheral surface in contact with both of said axially extending, circumferentially spaced surfaces, such that said eccentric rotation of said rotation plate will cause eccentric rotation of said drive pin, and contact of said rounded arcuate peripheral surface with said axially extending, circumferentially spaced surfaces will cause reciprocating rotation of said rotation cylinder through a limited angle about said axis of said rotation cylinder.

2. A tool as claimed in claim 1, wherein said casing includes a stepped portion through which extends said rotation cylinder, and said rotation cylinder has an outwardly extending annular flange adapted to abut said stepped portion to limit the extent of said axial movement of said rotation cylinder with respect to said casing.

3. A tool as claimed in claim 1, wherein said supporting means comprises a cylindrical support extending axially through said rotation cylinder, and means for fixing a dental drill within said cylindrical support.

4. A tool as claimed in claim 3, wherein said fixing means comprises at least one threaded aperture extending through said rotation cylinder, at least one aperture extending through said cylindrical support and in alignment with said threaded aperture, and screw means threaded through said threaded aperture and extending through said aperture for abutment with a dentral drill extending into said cylindrical support.

5. A tool as claimed in claim 4, comprising a plurality of said threaded apertures, said apertures and said screw means.

6. A tool as claimed in claim 4, wherein the width of said aperture is greater than the maximum outer diameter of said screw means.

7. A tool as claimed in claim 3, wherein adjacent ends of said rotation cylinder and said cylindrical support have mutually abutting flared portions which prevent relative axial movement between said rotation cylinder and said cylindrical support.

8. A tool as claimed in claim 7, wherein said flared portion of said rotation cylinder comprises an inner surface thereof which tapers axially and radially outwardly, and said flared portion of said cylindrical support comprises an outer surface thereof which tapers axially and radially outwardly.

* * * * *